United States Patent [19]

Tanigaki et al.

[11] Patent Number: 5,032,515
[45] Date of Patent: Jul. 16, 1991

[54] HYDROLYSIS PROCESS OF FAT OR OIL

[75] Inventors: Masanobu Tanigaki; Hidetoshi Wada; Masaru Sakata, all of Wakayama, Japan

[73] Assignee: Kao Corporation, Tokyo, Japan

[21] Appl. No.: 244,526

[22] Filed: Sep. 9, 1988

Related U.S. Application Data

[63] Continuation of Ser. No. 872,711, Jun. 10, 1986, abandoned.

[30] Foreign Application Priority Data

Jun. 14, 1985 [JP] Japan .................. 60-129612

[51] Int. Cl.⁵ .............. C12P 7/64; C12N 9/20; B01J 8/08; C12M 1/08
[52] U.S. Cl. .................. 435/134; 435/198; 435/314; 435/316; 422/227; 422/228; 422/231; 422/234; 422/256
[58] Field of Search ............... 435/134, 159, 198, 271, 435/314, 316, 315, 287, 288, 291, 813; 422/227, 234, 236, 228, 231, 256

[56] References Cited

U.S. PATENT DOCUMENTS

| | | | |
|---|---|---|---|
| 2,793,166 | 5/1957 | Hatch | 435/314 |
| 3,660,244 | 5/1972 | Che | 435/314 |
| 3,962,042 | 6/1976 | Malick | 435/314 |
| 4,204,042 | 5/1980 | Chelle | 435/314 |
| 4,256,839 | 3/1981 | Solomons et al. | 435/314 |

FOREIGN PATENT DOCUMENTS 0028483 2/1984 Japan .
0210893 11/1984 Japan .

OTHER PUBLICATIONS

Hoq et al., Agric. Biol. Chem. V. 49(11), 3171-8, 1985.
Hoq et al., JAOCS. V. 62(6), 1016-21, 1985.
Linfield et al., "Enzymatic Fat Hydrolysis and Synthesis", JAOCS, V. 61(2), 191-5, 1984.
Murakami et al., Yukagaku, V. 33(3), 148-50, 1984.
Murakami et al., Yukagaku, V. 32(9), 493-7, 1983.

Primary Examiner—Jacqueline Stone
Assistant Examiner—Gail Poulos
Attorney, Agent, or Firm—Flynn, Thiel, Boutell & Tanis

[57] ABSTRACT

Fat or oil is hydrolyzed with water and lipase effectively by supplying the fat or oil and water continuously each at a constant rate or semicontinuously in portions and simultaneously withdrawing a solution containing fatty acid(s) and an aqueous solution containing glycerol formed by the enzymatic reaction from the reaction system continuously at the same rates as those of the supplied fat or oil and water respectively or semicontinuously in portions to thereby maintain the glycerol concentration in the aqueous phase of the reaction system constant within a range of 10 to 40% by weight.

5 Claims, 2 Drawing Sheets

HYDROLYSIS PROCESS OF FAT OR OIL

This application is a continuation of U.S. Ser. No. 872,711, filed June 10, 1986 now abandoned.

This invention relates to a process for the hydrolysis of fat or oil. More particularly, it relates to a process for the hydrolysis of fat or oil with lipase, characterized by maintaining the glycerol concentration in the aqueous phase of the reaction system constant within a range of 10 to 40% by weight to thereby prevent inactivation of the lipase in the reaction system, thus efficiently hydrolyzing the fat or oil.

It has been known for a long time to hydrolyze fat or oil with lipase to produce glycerol and fatty acid(s). However there are many obstacles in an industrial application of the same. First the lipase is rapidly inactivated in general with the progress of the decomposition of the fat or oil so that it is impossible to recover the lipase for reuse. Thus it is inevitable to consume a large amount of the expensive enzyme. Therefore this process has no advantage from the viewpoint of cost compared with conventional hydrolysis at high temperature and pressure and the capability of the enzyme is not efficiently utilized at present.

Recently various attempts have been made to stabilize the enzyme and to recover the same for reuse. For example, we have found that the enzyme can be stabilized by maintaining the glycerol concentration in the aqueous phase of the reaction system within the range of 10 to 40% by weight throughout the hydrolysis (cf. Japanese Patent Application No. 13903/1985).

Glycerol, which stabilizes lipase, brings about a decrease in the hydrolysis ratio of fat or oil when employed in excess. Thus the glycerol concentration is maintained within 10 to 40% by weight in the process of Japanese Patent Application No. 13903/1985. This process is advantageous in stabilizing the enzyme as well as preventing decrease in the hydrolysis ratio. However the glycerol concentration adjusted to 10 to 15% by weight at the initial stage of the reaction rises to 20 to 30% by weight by the completion of the reaction. From the viewpoint of the hydrolysis ratio of the fat or oil, the lower concentration of glycerol is more desirable. That is, when glycerol is present in excess, the hydrolysis reaction proceeds in the reverse direction or attains an equilibrium as shown by the following formula, which results in a decrease in the hydrolysis ratio:

oil (fat) + water $\underset{\text{lipase}}{\overset{\text{lipase}}{\rightleftarrows}}$ fatty acid(s) + glycerol Accordingly it may be more suitable to continuously maintain the glycerol concentration at the minimum level required for stabilizing the enzyme than the process disclosed in Japanese Patent Application No. 13903/1985 wherein the glycerol concentration shows an increase in the last stage of the reaction, by taking into consideration the stability of the enzyme as well as the hydrolysis of the fat or oil.

SUMMARY OF THE INVENTION

We have studied to establish an enzymatic reaction system wherein the reaction proceeds while maintaining the glycerol concentration constant and found that our object can be achieved by controlling the supply of materials to the reaction system and the withdrawal of the oily and aqueous phases therefrom, thus completing the present invention.

Accordingly the present invention provides a process for the hydrolysis of fat or oil in a reaction system composed of the fat or oil, water and lipase, which is characterized by supplying the fat or oil and water to the reaction system continuously each at a constant rate or semicontinuously in portions and simultaneously withdrawing a solution containing fatty acid(s) and an aqueous solution containing glycerol formed by the enzymatic reaction continuously at the same rates as those of the fat or oil and water, respectively, or semicontinuously in portions to thereby maintain the glycerol concentration in the aqueous phase of the reaction system constant within a range of 10 to 40% by weight.

In the present invention, the ratio of the supplied fat or oil to water may be determined in the following manner.

Now an example wherein the glycerol concentration in the aqueous phase of the reaction system is to be maintained at 20% by weight will be illustrated.

Continuous or semicontinuous supply rate of fat (oil) = $X$ (kg/hr)

Continuous or semicontinuous supply rate of water = $Y$ (kg/hr)

Decomposition ratio of fat (oil) = $\eta$ (%)
Molecular weight of fat (oil) = $M$
Molecular weight of water = 18
Molecular weight of glycerol = 92

$$\frac{\frac{X}{M} \cdot \frac{\eta}{100} \cdot 92}{Y - 3 \cdot \frac{X}{M} \cdot \frac{\eta}{100} \cdot 18} = 0.2 \quad (1)$$

The ratio of X to Y can be determined from the above equation (1). For example, when M=900 and n=95%,

X/Y=1.84.

Thus the continuous or semicontinuous supply ratio of the fat or oil and water may be determined.

On the other hand, the amounts of the fat or oil and water supplied in a process wherein, for example, the enzyme, water and the fat or oil are mixed together by stirring may be determined by the volume of the oily phase in the reaction vessel. The theoretical residence time t of the fat or oil in the reaction vessel may be determined by the following equation:

$t = V/Q_1$ wherein
V = volume (m³) of oily phase in reaction vessel; and
$Q_1$ = supply rate (m³/hr) of fat or oil.

When the value of t is extremely small, the supply rate of the fat or oil and water exceeds the enzymatic reaction rate so that it becomes impossible to retain a sufficient residence time in the vessel for complete hydrolysis of the fat or oil. That is to say, the fat or oil supplied to the vessel is washed out without being completely hydrolyzed therein, which results in a decrease in the hydrolysis ratio of the same. The residence time theoretically required for a sufficient hydrolysis ratio of the fat or oil can not be defined since it varies depending on the amount of the enzyme, reaction temperature and other factors. It is generally at least five hours, preferably at least ten hours and more preferably at least 20 hours. (The supply ratio of the fat or oil and water is determined by the equation (1)).

Thus the continuous or semicontinuous supply of the fat or oil and water makes it possible to maintain the glycerol concentration in the aqueous phase of the reaction system constant. However an extremely large reaction vessel is required unless the fatty acid(s) and glycerol formed by the reaction are successively withdrawn from the reaction system. Therefore it is preferable to carry out this process in a continuous manner. The amounts of the fatty acid solution and the aqueous solution of glycerol to be withdrawn should be the same as those of the supplied fat or oil and water, respectively.

Since the reaction system comprises a water/oil emulsion, it is necessary to take out a fatty acid(s) solution and an aqueous solution of glycerol, each free from emulsion, therefrom in order to withdraw these two solutions. This may be carried out by centrifugation, membrane separation or static separation. When the fatty acid solution and the aqueous solution of glycerol, each free from emulsion, are to be efficiently taken out by static separation, it is necessary to allow the reaction system to stand for a long time or to heat the same to approximately 60° C. or above. However these two procedures are undesirable since the former is unsuitable for continuous performance while the latter results in inactivation of the enzyme by heating. Thus it is preferable to carry out the separation by centrifugation or membrane separation. The emulsion may be divided into three phases consisting of an oily phase, i.e. a fatty acid(s) solution, an emulsion phase and an aqueous phase, i.e. an aqueous solution of glycerol.

Among these three phases, the emulsion phase generally contains approximately 80 to 95% of the enzyme and the aqueous phase contains approximately 5 to 20% of the same, although these contents vary depending on temperature. In the process of the present invention, it is preferable to return the entire amount of the emulsion phase and the enzymatic solution obtained by concentrating and recovering the aqueous phase with the use of an ultrafiltration membrane, i.e. an ultrafiltration concentrate, to the reaction system to thereby recycle the enzyme.

In the case of centrifugation, the top is the oily phase, the medium is the emulsion phase and the bottom is the aqueous phase. The whole amount of the medium emulsion phase is returned to the reaction system. The aqueous phase is treated by ultrafiltration. The centrifugation may be carried out either continuously or batchwise. In the latter case, the reaction system is centrifuged batchwise in portions. Thus the fatty acid solution and the aqueous solution of glycerol are semicontinuously withdrawn.

On the other hand, in the case of membrane separation, the fatty acid solution and the aqueous solution of glycerol each free from emulsion may be obtained by filtering the emulsion solution through separating membranes each having a pore size smaller than the particle size of the emulsion.

The pore size of the separating membranes can not be defined as a rule since the particle size of the emulsion varies depending on various factors including the form of the stirrer in the reaction vessel and the stirring rate. It is generally appropriate to employ an average pore size of 0.01 to 5 $\mu$m, preferably 0.05 to 2 $\mu$m. It is preferable to carry out the ultrafiltration under a pressure of 2 kg/cm$^2$ or below since a higher pressure would result in serious clogging. When the oily phase is to be separated, it is preferable to use a membrane made of a material having a small interfacial tension between oils, such as hydrophobic polymers including Teflon, polysulfone, polyethylene and polypropylene, ceramics or metals such as stainless steel or aluminum. In such a case, it is preferable to immerse the separating membrane in a pure oil prior to the use in filtration in order to obtain the oily phase in purer form. When the aqueous phase is to be separated, it is preferable to use a membrane made of a material having a small interfacial tension between the membrane material and water, such as hydrophilic polymers including polyacrylonitrile, cellulose acetate, polyamide and polyurethane, ceramics or metals such as stainless steel or aluminum. In such a case, it is preferable to immerse the separating membrane in water prior to the use in filtration in order to obtain the aqueous phase in purer form. The form of the membrane is not restricted so that it may be in any form such as flat sheet, tube, spiral or hollow fiber.

When a membrane for separation of the aqueous phase is an ultrafiltration membrane having a fractionating molecular weight of about 3,000 to 20,000 and being formed from the above listed starting material, the ultrafiltration membrane for recovering of an enzyme used as disclosed below may not be used.

As described above, the aqueous phase obtained by centrifugation or membrane separation contains 5 to 20% of the added enzyme. Accordingly it is necessary to recover the enzyme dissolved therein. This recovery is preferably carried out with the use of an ultrafiltration membrane. In the recovery of the enzyme from the aqueous phase, any ultrafiltration membrane may be employed without restricting the material, form or the properties thereof so long as the enzyme can not pass therethrough. For example, it may be made of any material such as cellulose acetate, polyacrylonitrile, polysulfonate or polyamide and in any form such as flat sheet, tube, spiral or hollow fiber. The fractionating molecular weight of the ultrafiltration membrane is preferably from about 3000 to 20000. The use of such an ultra-filtration membrane for separation of the aqueous phase will save use of an ultrafiltration membrane for recovery of the enzyme as described below. By the ultra-filtration, the aqueous solution of glycerol free from the enzyme permeates through the membrane while a concentrated solution of the enzyme remains therein and is preferably returned to the reaction system. The enzyme solution is concentrated at least fivefold, preferably at least 20-fold.

As described above, 5 to 20% of the introduced enzyme is dissolved in the aqueous solution of glycerol. Therefore it is also possible to add fresh enzyme as a substitute for the dissolved enzyme instead of performing the ultrafiltration.

Figure 1:
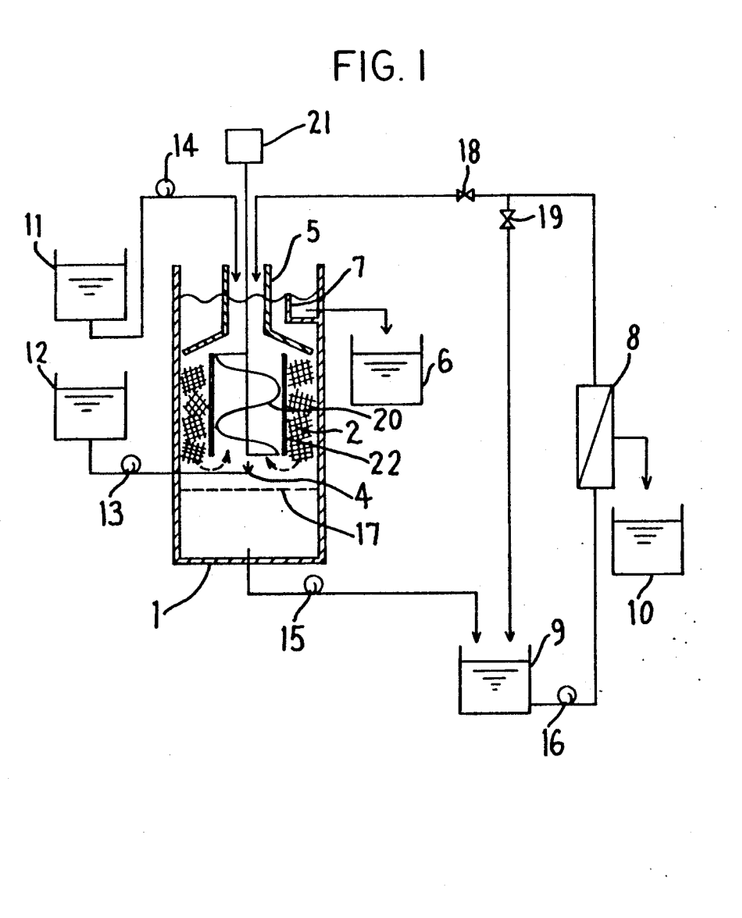
FIG. 1 is a schematic view of a system for performing the hydrolysis reaction.
Figure 2:
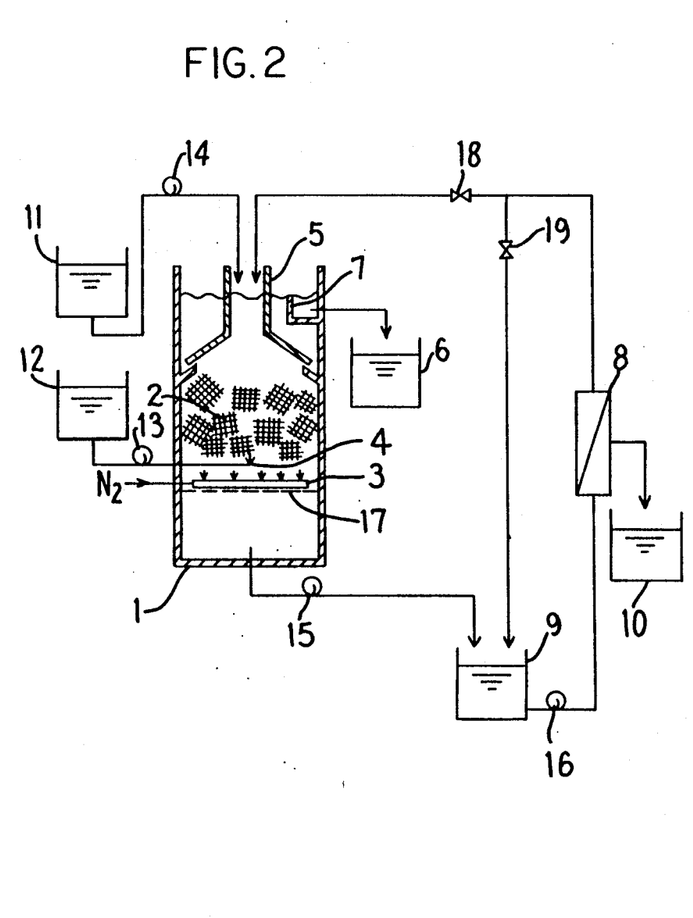
FIG. 2 is a view like FIG. 1 and showing a modified system.
Figure 3:
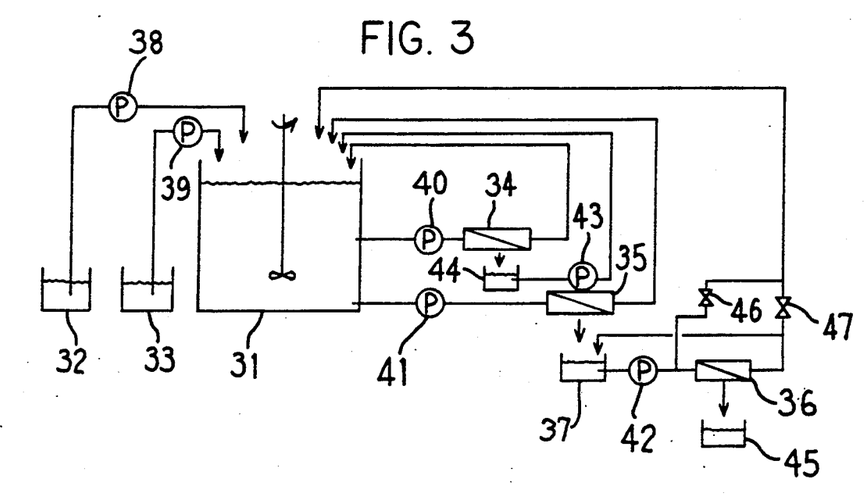
FIG. 3 is a schematic view of a system employing membrane separation.
Figure 4:
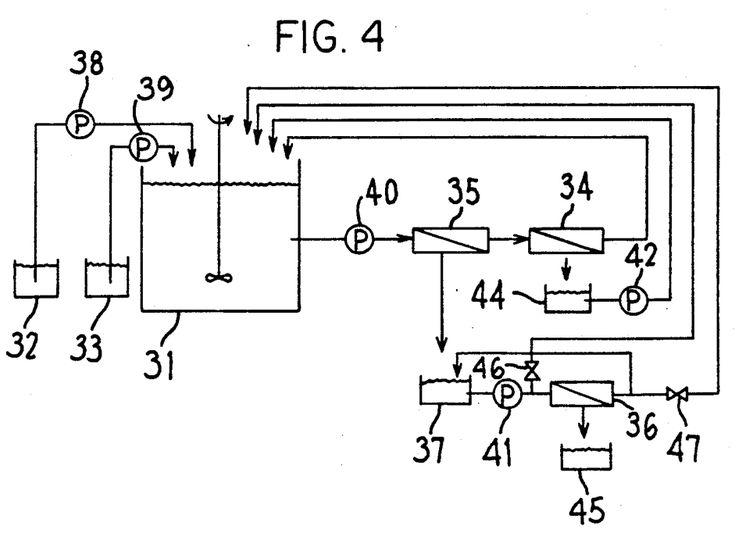
FIG. 4 is a view like FIG. 3 and showing a modification.

In FIGS. 1 and 2, the reference numerals identify elements as follows:
1—reactor;
2—packing;
3—nozzle for blowing $N_2$ gas;
4—nozzle for supplying substrate (non-aqueous solution phase);
5—upper baffle;
6—tank for product (non-aqueous solution phase);
7—weir;
8—ultrafiltration membrane;
9—tank for treating aqueous phase with membrane;
10—tank for product (aqueous phase);
11—tank for substrate (aqueous phase);
12—tank for substrate (non-aqueous solution phase)
13 to 16—pumps;
17—lower baffle;
18 and 19—valves;
20—stirring blades; and
22—draft tube FIG. 3 and FIG. 4 show an embodiment of the invention in which oil or fat is hydrolyzed with lipase, used in Examples 9 and 11.

In FIGS. 3 and 4, the reference numerals identify elements as follows:
31 is a reaction vessel;
32 is an oil tank;
33 is a water tank;
34 is a separating membrane for fatty acid solution;
35 is a separating membrane for aqueous solution of glycerol;
36 is an ultrafiltration membrane;
37 is a tank for aqueous solution of glycerol;
38 to 43 are pumps;
44 is a tank for fatty acid solution;
45 is a tank for aqueous solution of glycerol; and
46 and 47 are valves.

FIGS. 3 and 4 each illustrate and explain a reaction system of the invention using the membrane separation. A membrane 34 to separate a fatty acid solution and that 35 to separate an aqueous solution of glycerol may be aligned, either in parallel as shown in FIG. 3 or in series as shown in FIG. 4. When the membranes are aligned in series, it is preferable to place the membrane 35 in front of the membrane 34 whereby to elevate a ratio of the oil phase to the aqueous phase in feeding prior to feeding to the membrane 34. This way a permeation extent of the fatty acid solution through the membrane 34 is increased.

These embodiments as shown in FIGS. 3 and 4 show use of a reaction vessel. More than one reaction vessel may be used in the invention.

The abovementioned process makes it possible to stably recover and reuse the enzyme. Furthermore, in the process of the present invention, the enzyme can be readily recovered and reused without being inactivated even at a high temperature. Generally speaking, enzymes are very unstable to heat, not excepting lipase which shows a gradual decrease in the activity at a temperature exceeding 40° C. Accordingly there have been widely attempted procedures to develop a thermostable lipase. However, the process of the present invention makes it possible to prevent inactivation of conventional lipase, which is liable to be inactivated at a high temperature, to thereby stably reuse the same without employing such a thermostable lipase. That is, the process of the present invention gives a high hydrolysis ratio of fat or oil, i.e. 80 to 90%, at a temperature of as high as 45° to 50° C. and yet the enzyme can be recovered and reused. Thus fat or oil which is solid at room temperature, e.g. beef tallow or palm oil, may be efficiently hydrolyzed by the process of the present invention with the use of the enzyme. Furthermore since the process of the present invention may be carried out at a high temperature, the hydrolysis rate of fat or oil is elevated. Therefore it is possible to hydrolyze a larger amount of fat or oil at this temperature in a definite period of time than in a reaction at a lower temperature.

The invention may be worked in the below shown manner in reference to FIGS. 1 and 2. This is a preferable embodiment of the invention.

For example, an enzymatic reaction system of $A+B \rightarrow C+D$, wherein A and B are substrates and C and D are reaction products and A and C are soluble in water while B and D are insoluble in water, will be illustrated with reference to FIG. 1 in which reactor 1 is equipped with a draft tube 22.

The aqueous phase and the non-aqueous solution are introduced into the reactor at a given ratio thereof. Then the aqueous phase having been present in the bottom is lifted with stirring blades 20 provided in the draft tube 22 to form an emulsion, perform the close contact between the emulsion and the enzyme and then carry out the enzymatic reaction.

In the example shown in FIG. 1, a packing 2 is charged around the draft tube 22 in order to increase the efficiency of the contact between the substrates and the enzyme and maintain the enzyme with a high efficiency of retention. If these requirements are met, the packing 2 will not be needed.

It is preferable that baffles 5, 17 are provided at the upper and lower portions of the reactor to prevent both phases from completely mixing with each other and form a separation part there in which the aqueous phase and the non-aqueous phase are separated from each other.

According to the embodiment, the products can be separated from the reaction mixture while the reaction proceeds. The continuous separation can be performed. In addition, the separation of the products and feeding of the reactants can be effected at the same time, continuously or semi-continuously.

In the reactor, most of the enzyme used in the reaction is retained in the packing layer 2. Further it is preferable to concentrate and recover the enzyme dissolved in the aqueous phase and then re-use it effectively. For the purpose, an ultrafiltration membrane may be used. Any membrane 8 may be used so long as the enzyme does not permeate therethrough. Suitable membrane materials include cellulose acetate, polyacrylonitrile, polysulfone and polyamide. Suitable membrane forms include a flat sheet, a tube, a spiral and a hollow fiber. The membrane 8 is not limited in view of its fractionating molecular weight so long as it prevents permeation of the enzyme. Practically it is preferred to have a fractionating molecular weight of 3,000 to 50,000.

According to the ultrafiltration, the aqueous phase free from the enzyme is continuously removed out and the concentrated liquid containing the enzyme is returned to the reaction system, continuously or semi-continuously.

When most of the enzyme used is kept in the reactor 1 and the enzyme is dissolved only in a negligible amount, the separation of the enzyme by ultrafiltration will not be required. Alternatively, an immobilized enzyme may be used and packed in the reactor without requiring the recovery step of the enzyme, such as ultrafiltration. Moreover the ultrafiltration may not be used if a fresh enzyme is added to the reactor so as to correspond to the amount of enzyme which has been dissolved in the aqueous phase.

According to the invention method, an enzyme can be retained in a reactor and recovered with a high efficiency without any special pre-treatment thereof. For this purpose, an enzyme may be retained by adsorption on a packing material without a pre-treatment. It may be packed in an immobilized form prepared by a conventional immobilizing method. Instead it may be used as it is. Selection of the most suitable method will depend on the properties of an enzyme to be used and reaction conditions.

In the embodiment shown in FIG. 1, the draft tube may be used with any diameter. The diameter may be selected to conform with reaction conditions. It is preferred to be a value corresponding to 5 to 90 percent of the diameter of the reactor. The stirring blades may be operated with such a rotation rate that the lower phase in the reactor 1 may be effectively lifted, a desired mixing may be performed around the interface between the oil phase and the aqueous phase and in addition the oil phase and the aqueous phase may be left separately as they are at the upper portion and the lower portion in the reactor 1, respectively.

A packing material 2 is used in the embodiment shown in FIG. 1. Any type of packing is available to the invention. It conventionally includes Raschig rings, Lessing rings, Berl saddles, Intalox saddles, Paul rings and a cylindrical net. It may be made of metal, ceramic or plastic.

Immobilization of an enzyme may be conducted in a conventional manner, including the covalent bonding method, the crosslinking method, the inclusion method and a combination method thereof.

In order to lift the aqueous phase upward from the lower part in the reactor, any method may be selected so long as it is suitable for the reaction conditions and the upper layer and the lower layer are mixed with each other around the interface thereof. For example, a method using the draft tube 22 as shown in FIG. 1, may be conducted. An inert gas, such as nitrogen gas, is blown up from a position 3 lower than the interface of both layers, as seen in FIG. 2. An inert gas, such as nitrogen gas, can be introduced into the draft tube 22 as seen in FIG. 1. Stirring around the interface is effective without use of a draft tube.

As disclosed above about the embodiment of the invention, the upper layer and the lower layer are mixed with each other around the interface therebetween and on the other hand, they are left as they are, respectively, at the top portion and the bottom portion of the reactor. The reaction proceeds in this way. In the process, the oil phase and the aqueous phase can be advantageously removed out separately while the reaction proceeds and the intended products can be eventually obtained. This way the process can be continuously effected with substrates fed continuously and the reaction products removed continuously at the same time. The continuous process can be conducted so that each ingredient may have a constant concentration in the reaction. The enzyme used in the process can be stable advantageously.

It is noted that the stability of a lipase depends on the concentration of glycerin, in the hydrolysis of oil or fat with the lipase. In the invention, when the concentration of glycerin in the aqueous phase is in the range between 10 and 40 percent by weight, the enzyme used is effectively stabilized and the hydrolysis proceeds advantageously.

The above shown embodiment, also illustrated in FIGS. 1 and 2, enables each ingredient to be controlled at a constant concentration without any difficulty and the hydrolysis of oil or fat with the lipase can proceed effectively. For this purpose, a suitable feeding ratio of oil or fat to water is determined and the concentration of glycerin is kept constant at a suitable value according to the method discussed herein.

The method can apply to a reaction in which two dispersion phases of an aqueous phase and a non-aqueous phase, including a hydrophobic phase which is not soluble or is difficulty soluble in water, are involved, such as an enzymatic reaction and a microbial reaction. In addition to the example of the invention in which oil or fat is hydrolyzed with a lipase, for instance, the method may be used for a synthesis of a triglyceride with lipase, an ester-exchanging reaction of a triglyceride and syntheses of peptides with protease such as synthesis of aspartame (aspartylphenylalanine methyl ester) from carobenzyloxy-1-aspartic acid and α-phenylalanine methyl ester with thermolysin and dehydration or hydroxylation with a microbe. In other words, the method substantially applies to the two phase reaction in which one phase comprises a substrate or a product which not is soluble or difficulty soluble in water and the other phase comprises another substrate or another product which is soluble in water. It will extend to other applications.

The above shown method is so advantageously effective that an enzyme or a microbe may be used in the immobilized form, it may be used with a suitable packing, not immobilized, or it may be retained in a reactor to a certain extent without use of a packing. The enzyme and microbe can be effectively recovered with use of an ultrafiltration membrane, even through they have been dissolved in the aqueous phase. For this reason, they can be recovered without a complicated immobilization step. The enzyme and microbe recovered can be used again.

The invention successfully accepts use of an enzyme and microbe which have not yet been purified to a high extent. An extract liquid, a partially purified product and a fermentation liquid can be used as they are.

FIGS. 1 and 2 illustrate an embodiment in which one reactor is used. Moreover the invention can be worked with a plurality of reactors to perform a multistage reaction move effectively.

The lipase used in the present invention is not strictly limited. General examples thereof are those derived from microbes belonging to the genera of, for example, Candida, Chromobacterium, Aspergillus, Penicillium, Mucor, Geotrichum, Thizopus, Arthrobacter and Phycomyces; those obtained from animal organs such as pancreas; and those obtained from vegetable seeds such as castor seed. The purity of these enzymes is not strictly limited so that not only purified enzyme specimens but also unpurified products may be employed.

Examples of the fat or oil used in the present invention are vegetable oils such as soybean oil, palm oil, coconut oil, olive oil, linseed oil, castor oil and tung oil and animal fats and oils such as beef tallow, lard and fish oil.

As described above, the present invention provides a novel process of an enzymatic reaction wherein the glycerol concentration in the aqueous phase of the reaction system is maintained constant by carrying out a continuous or semicontinuous reaction to thereby stabilize the enzyme and prevent a decrease in the decomposition ratio. Consequently the process of the present invention exhibits many advantages such that a high decomposition ratio can be maintained, that the enzyme can be reused and that the reaction can be performed at a high temperature, thus solving the problems encountered in conventional methods.

EXAMPLES

To further illustrate the present invention, and not by way of limitation, the following Examples will be given.

EXAMPLE 1

Soybean oil was hydrolyzed with lipase in a reaction system as shown in FIG. 1. In the case of the hydrolysis of fat or oil with lipase, 4 is a nozzle for supplying the fat or oil, 6 is a tank for a fatty acid solution, 9 is a tank for treating an aqueous solution of glycerol with a membrane, 10 is a tank for aqueous glycerol and 11 is a water tank, each in FIGS. 1 and 2. 1kg of hydrolyzed fatty acids obtained by previously hydrolyzing soybean oil with enzyme(s) and containing 85% of fatty acids, 1 kg of a 20% by weight aqueous solution of glycerol and 2 g (320000U/g) of lipase produced by Candida cylindracea were introduced into a reactor 1 and the reaction was carried out while maintaining the reactor at 30° C. The ratio of the diameter of the reactor 1 to that of draft tube 22 was 10:6. Stirring was performed with ribbon blades as shown in FIG. 1 at a rate of approximately 0.5 m/sec.

Soybean oil containing 0% of fatty acids was continuously supplied from an oil tank 12 to the reactor 1 with a pump 13 at a flow rate of 50 g/hr through the bottom of the reactor. Separately water was continuously supplied from a water tank 11 to the reactor 1 through a pump 14 at a flow rate of 25 g/hr through the top of the reactor. Thus the average residence time of the soybean oil in the reactor was adjusted to 20 hr and the glycerol concentration in the aqueous phase was maintained at approximately 20%. Water present in the lower part of the reactor 1 was lifted with the draft tube 22. The lipase, the oil and water came into contact with each other while water drops passed through the packing layer around the draft tube 22.

On the other hand, baffles 5 and 17 were provided at the upper and lower parts of the reactor, respectively, to thereby give fatty acids almost free from water and aqueous solution of glycerol almost free from the oil. Thus the fatty acids were continuously withdrawn at the same rate as that of the supplied oil by overflowing the baffle 5. On the other hand, the aqueous solution of glycerol was continuously withdrawn from the bottom of the reactor with a pump 15 and stored in a tank 9 followed by subjecting the aqueous solution to ultrafiltration with a membrane 8 to thereby concentrate and recover the enzyme dissolved in the aqueous phase. The aqueous glycerol was withdrawn at a rate controlled to 25 g/hr. In this Example, a polyacrylonitrile membrane having a fractionating molecular weight of 30000 was employed as the ultrafiltration membrane 8 and the enzyme was semi-continuously concentrated and returned to the reactor.

The reaction was continued in the reaction system as described above while continuously supplying soybean oil and water and continuously withdrawing the fatty acid solution and the aqueous solution of glycerol.

After 20 hours corresponding to the average residence time in the reactor, the fatty acid solution was collected from the fatty acid solution tank 6 and the acid value and saponification value of the same were determined. As a result it was found that the acid value was 170 while the saponification value was 194. The hydrolysis ratio calculated according to the following equation was 86%:

$$\text{hydrolysis ratio of oil (\%)} = \frac{\text{acid value}}{\text{saponification value}} \times 100$$

The glycerol concentration in the tank 10 for the aqueous solution of glycerol was 20% by weight.

Similarly the hydrolysis ratio and the glycerol concentration were determined 40, 60, 80 and 100 hours after the initiation of the supply of soybean oil Table 1 shows the result.

TABLE 1

| Reaction period (hr) | 20 | 40 | 60 | 80 | 100 |
|---|---|---|---|---|---|
| Hydrolysis ratio (%) | 86 | 85 | 86 | 85 | 85 |
| Glycerol concentration (%) | 20 | 19 | 18 | 19 | 19 |

Thus the enzyme was by no means inactivated after continuously performing the reaction for 100 hours and the hydrolysis ratio of soybean oil was maintained at 85 to 86%. Similarly the glycerol concentration in the aqueous phase was maintained at 18 to 20%.

On the other hand, the water content of the fatty acid solution obtained in the tank 6 was lower than 0.5%. The aqueous glycerol permeating through the ultrafiltration membrane 8 exhibited an excellent quality. Therefore it was found that this reaction system made it possible to separate the reaction products simultaneously with the progress of the reaction, to efficiently recover and reuse the enzyme and to maintain a high hydrolysis ratio.

EXAMPLE 2

The same reaction system as the one used in Example 1 was employed. The amount of the hydrolyzed soybean oil initially introduced into the reactor as well as those of the 20% by weight aqueous solution of glycerol and the enzyme were the same as those used in of Example 1, but the supply rates of the soybean oil and water continuously supplied with pumps 13 and 14, respectively, were changed to be as follows:
soybean oil—25 g/hr; and
water—12.5 g/hr.
Thus the average residence time of the soybean oil was determined to be 40 hours.

The fatty acid solution was withdrawn by overflowing the baffle 7 while the aqueous glycerol was withdrawn by controlling the rate to 12.5 g/hr. Thus the hydrolysis was performed continuously. The hydrolysis ratio of the soybean oil and the glycerol concentration were determined 40, 80 and 120 hours after the start of the hydrolysis reaction. Table 2 shows the result.

TABLE 2

| Reaction period (hr) | 40 | 80 | 120 |
|---|---|---|---|
| Hydrolysis ratio (%) | 90 | 89 | 90 |
| Glycerol concentration (%) | 17 | 18 | 18 |

Thus it was found that the hydrolysis ratio reached approximately 90% by adjusting the residence time to 40 hours.

EXAMPLE 3

In Example 1, the water in the reactor 1 was lifted with the stirring blades 20 in the draft tube 22 to thereby perform the hydrolysis. In this Example, a nitrogen gas was blown from the bottom of the reactor as shown in FIG. 2 to thereby lift water drops into the oily phase and to contact the lipase retained in the packing layer with the oil and water, thus performing the hydrolysis. An inverted funnel-type baffle 5 was provided at the upper part of the reactor in order to collect the nitrogen to thereby prevent the solutions from mixing together above the baffle.

The amounts of the hydrolyzed soybean oil, the 20% by weight aqueous solution of glycerol and the enzyme were the same as those of Example 1. Further the average residence time of the soybean oil was the same as that of the Example 1. Thus soybean oil was continuously hydrolyzed by blowing the nitrogen gas at a rate of 100 ml/min. The hydrolysis ratio of the soybean oil and the glycerol concentration were determined 20, 40 and 60 hours after the start of the hydrolysis reaction. Table 3 shows the result.

TABLE 3

| Reaction period (hr) | 20 | 40 | 60 |
|---|---|---|---|
| Hydrolysis ratio (%) | 86 | 85 | 86 |
| Glycerol concentration (%) | 17 | 18 | 18 |

Thus it was found that the process comprising blowing nitrogen gas from the bottom of the reactor gave a similar effect to that obtained by stirring as shown in FIG. 1. That is, the process of this Example made it possible to maintain the hydrolysis ratio at 85 to 86%, which suggested that the separation of the fatty acid solution phase and the aqueous phase of glycerol was efficiently carried out like in the case of Example 1.

EXAMPLE 4

In Examples 1, 2, and 3, each continuous hydrolysis was performed with the use of a single reactor 1. On the other hand, two-stage continuous hydrolysis was carried out with the use of two reactors as shown in FIG. 2 in order to efficiently give a high hydrolysis ratio.

In this case, the soybean oil was supplied in such a manner as to flow countercurrent to the to water. That is, the soybean oil was first supplied to the reactor in the first stage and the fatty acid solution thus obtained was supplied again to the reactor in the second stage. On the other hand, water was supplied while controlling the glycerol concentration in the reactors to approximately 20%.

The soybean oil was supplied at a rate of 50 g/hr. A mixture of fresh water and the aqueous glycerol recovered from the reactor in the second stage having a concentration of approximately 15% was supplied to the reactor in the first stage at a rate of 3 g/hr while a mixture of the aqueous glycerol recovered from the reactor in the first stage and fresh water was supplied to the reactor in the second stage at a rate of 20 g/hr.

The hydrolysis ratio of the soybean oil and the glycerol concentration were determined at each point. Table 4 shows the result.

TABLE 4

| Reaction period (hr) | 20 | 40 | 60 |
|---|---|---|---|
| 1st stage | | | |
| Hydrolysis ratio (%) | 85 | 86 | 85 |
| Glycerol concentration (%) | 20 | 19 | 20 |
| 2nd stage | | | |
| Hydrolysis ratio (%) | 93 | 93 | 93 |
| Glycerol concentration (%) | 23 | 24 | 23 |

EXAMPLE 5

The reaction system is shown in FIG. 3.

3 l of hydrolyzed fatty acids obtained by previously hydrolyzing soybean oil with enzymes and containing 85% of fatty acids, 1.5 l of a 20% by weight aqueous solution of glycerol and 1.5 g (320000U/g) of lipase produced by Candida cylindracea were added to a reaction vessel 31 equipped with a stirrer and stirred therein while maintaining the reaction vessel at 30° C.

Soybean oil was continuously supplied to the reaction vessel 31 from an oil tank 32 with a pump 38 at a flow rate of 0.15 l/hr while water was continuously supplied to the reaction vessel 31 from a water tank 33 with another pump 39 at a flow rate of 0.08 l/hr. The soybean oil and water thus supplied were mixed together by stirring in the reaction vessel. Thus an enzymatic reaction was performed at a reaction temperature of 30° C. A water/oil emulsion was formed in the reaction vessel thereby.

The emulsion in the reaction vessel 31 was supplied by a pump to a separating membrane 34 for fatty acids, which was made of polyolefin and had an average pore size of 0.2 $\mu$m and a membrane area of 0.2 m$^2$, under an inlet pressure of 1 kg/cm$^2$. The solution permeating through the membrane filter 34 was a fatty acid solution free from water and the enzyme. The membrane filter 34 had been previously immersed in soybean oil. The solution obtained from the outlet of the filter was returned to the reaction vessel 31. The average permeation rate of the filter-permeable fatty acid solution was 0.4 l/hr. Since this rate exceeded the supply rate of the soybean oil, i.e. 0.15 l/hr, the permeated fatty acid solution was temporarily stored in a tank 44 for the fatty acid solution and then returned to the reaction vessel 31 at an average flow rate of 0.25 l/hr.

On the other hand, the aqueous phase in the reaction vessel 31 was supplied by a pump 41 to a separating membrane 35 for the aqueous solution of glycerol, which was a ceramic filter and had an average pore size of 1.5 $\mu$m and a membrane area of 0.015 m$^2$, under an inlet pressure of 1 kg/cm$^2$. The obtained solution which had permeated through the ceramic filter was an aqueous solution of glycerol free from oil. This filter had been previously immersed in water. The solution obtained from the outlet of the filter was returned to the reaction vessel 31. The average permeation rate of the aqueous solution of glycerol was 2.3 l/hr. The solution which had permeated through the filter was stored in a tank for the aqueous solution of glycerol 37 and supplied to an ultrafiltration membrane 36 which was made of polyacrylonitrile and had a fractionating molecular weight of 13000 and a membrane area of 0.2 m$^2$, with a pump 42 to thereby concentrate and recover the enzyme. The rate of the solution permeating through the ultrafiltration membrane 36 was maintained at the same level as the supply rate of the water to the reaction vessel, i.e. 0.08 l/hr, by controlling the pressures of the pump 42 and a valve 46. The solution permeating through the ultrafiltration membrane, which was an aqueous solution of glycerol free from the enzyme, was stored in a tank 45, while a portion (0.01 l/hr) of the solution obtained from the outlet of the ultrafiltration membrane 36 was returned to the reaction vessel 31. The solution thus returned was a concentrate of the enzyme in the aqueous solution of glycerol.

With the use of this reaction system, the reaction was continued while continuously supplying soybean oil and water and continuously withdrawing the fatty acid solution and the aqueous solution of glycerol.

After 20 hours, which corresponded to the theoretical residence time in the reaction vessel, the fatty acid solution was collected from the tank for the fatty acid solution 44 and the acid and saponification values of the same were determined. Consequently it was found that the acid value thereof was 175 while the saponification value thereof was 194. The hydrolysis ratio calculated by the following equation was 90%:

$$\text{hydrolysis ratio of oil} = \frac{\text{acid value}}{\text{saponification value}} \times 100$$

The glycerol concentration in the aqueous solution of glycerol in the tank 45, was 20% by weight.

Similarly the hydrolysis ratio and the glycerol concentration were determined 40, 60, 80 and 100 hours after the initiation of the supply of the soybean oil. Table 5 shows the results.

TABLE 5

| Reaction period (hr) | 20 | 40 | 60 | 80 | 100 |
|---|---|---|---|---|---|
| Hydrolysis ratio (%) | 90 | 91 | 89 | 90 | 90 |
| Glycerol concentration (%) | 20 | 19 | 19 | 19 | 19 |

Thus the enzyme was by no means inactivated even after the continuous reaction for 100 hours and the hydrolysis ratio of the soybean oil was maintained at 89 to 91% throughout the reaction period. Further the glycerol concentration in the aqueous phase was maintained at 19 to 20% by weight therethrough.

COMPARATIVE EXAMPLE 1

The same reaction system as the one described in Example 5 was used. The amount of the hydrolyzed soybean oil initially introduced and the amount of the introduced 20% by weight aqueous solution of glycerol and that of the enzyme were the same as those of Example 5 but the amounts of the soybean oil and water continuously added with pumps 38 and 39, respectively, were changed as follows:
soybean oil—0.3 l/hr; and
water—0.16 l/hr (theoretical residence time = 10 hr).

The enzymatic reaction was continued at 30° C. under continuous stirring similar to Example 5. The fatty acid solution and the aqueous solution of glycerol formed by the enzymatic reaction were withdrawn at rates of 0.3 l/hr and 0.16 l/hr, respectively, each similar to the corresponding supply rate. Since the average permeation rate of the fatty acid solution through the membrane filter 34 was 0.4 l/hr, a portion (0.1 l/hr) thereof was returned to the reaction vessel 31 with the pump 43. On the other hand, since the average permeation rate of the aqueous solution of glycerol through the membrane 35 was 2.3 l/hr, the permeation rate thereof through the ultrafiltration membrane 36 was adjusted to 0.16 l/hr by controlling the pressures of the valve 46 and the pump 42. Thus the reaction was continuously carried out and the hydrolysis ratio of the soybean oil and the glycerol concentration were determined 10, 20, 40 and 60 hours after the start of the hydrolysis reaction. Table 6 shows the results.

TABLE 6

| Reaction period (hr) | 10 | 20 | 40 | 60 |
|---|---|---|---|---|
| Hydrolysis ratio (%) | 83 | 79 | 72 | 65 |
| Glycerol concentration (%) | 19 | 17 | 15 | 14 |

Thus the hydrolysis ratio of the oil gradually decreased by shortening the theoretical residence time to 10 hours.

EXAMPLE 6

In Comparative Example 1, the hydrolysis ratio of the oil gradually decreased when the theoretical residence time was short, i.e. 10 hours. In this Example, the reaction temperature was raised and the amount of the enzyme was increased while the theoretical residence time was maintained short, i.e. 10 hours. That is, the reaction temperature was raised to 45° C. and the amount of the added enzyme was increased to 12 g. The hydrolysis reaction was continued under the same condition as that of Comparative Example 1 except those as described above. Table 7 shows results.

TABLE 7

| Reaction period (hr) | 10 | 20 | 40 | 60 | 100 |
|---|---|---|---|---|---|
| Hydrolysis ratio (%) | 90 | 90 | 92 | 91 | 90 |
| Glycerol concentration (%) | 20 | 19 | 19 | 19 | 19 |

Thus it was found that increases in the enzyme concentration and reaction temperature would accelerate the enzymatic reaction. Accordingly the added oil was thoroughly hydrolyzed within the residence time without any decrease in the hydrolysis ratio even though the amount of the added oil was large, in other words, even though the residence time in the reaction vessel was short.

EXAMPLE 7

A reaction system as shown in FIG. 4 was employed. A separating membrane for a fatty acid solution and that of an aqueous solution of glycerol were arranged in series. An aqueous solution containing glycerol was withdrawn with the membrane 35 while an oily solution containing fatty acids alone was withdrawn with the membrane 34. The membrane 35 was a ceramic filter having an average pore size of 1.5 μm and a membrane area of 0.015 m² and had been previously immersed in water, while the membrane 34 was the same ceramic filter which had been previously immersed in soybean oil.

3 l of hydrolyzed fatty acids containing 85% of fatty acids, 2 l of a 15% by weight aqueous solution of glycerol and 1.5 g of the same enzyme as the one used in Example 5 were introduced into a reaction vessel 31 and stirred therein in the same manner as in Example 5. Soybean oil and water were supplied with a pump 38 at a rate of 0.075 l/hr and with a pump 39 at a rate of 0.05 l/hr, respectively, with a theoretical residence time of 40 hours. The reaction was continued at 30° C. under stirring. On the other hand, an aqueous solution of glycerol and a fatty acids solution were separated from the emulsion in the reaction vessel 31 with membranes 35 and 34, respectively, and the residual emulsion was returned to the reaction vessel 31. The average permeation rate of the fatty acid solution through the membrane 34 was 0.15 l/hr while that of the aqueous solution of glycerol through the membrane 35 was 1.7 l/hr. The aqueous solution of glycerol permeating through the membrane 35 was supplied to an ultrafiltration membrane 36 which was made of polysulfone and had a fractionating molecular weight of 6,000 and a membrane area of 0.2 m, to thereby collect the enzyme dissolved in the aqueous solution of glycerol. The permeation rates of the fatty acid solution and the aqueous solution of glycerol through the membranes 34 and 36, respectively, were adjusted to the same as those of at pumps 38 and 39, respectively, by controlling pumps 42 and 41 and a valve 46. The excessive fatty acid solution and aqueous solution of glycerol were returned to the reaction vessel 31.

Thus the reaction was continued while continuously supplying and withdrawing for a theoretical residence time of 40 hours and the hydrolysis ratio of the oil and the glycerol concentration in the aqueous phase were determined 40, 80, 120 and 160 hours after the start of the hydrolysis reaction. Table 8 shows the results.

TABLE 8

| Reaction period (hr) | 40 | 80 | 120 | 160 |
|---|---|---|---|---|
| Hydrolysis ratio (%) | 90 | 90 | 92 | 91 |
| Glycerol concentration (%) | 15 | 14 | 14 | 14 |

Thus the enzyme was stable at 15% by weight glycerol concentration, in the aqueous phase of the reaction system and a high hydrolysis ratio of the oil was obtained throughout a long period of time.

COMPARATIVE EXAMPLE 2

The same reaction system as in Example 7 was employed. The reaction was carried out by adjusting the glycerol concentration in the aqueous phase of the reaction system to 5% by weight. That is 3 l of hydrolyzed fatty acids containing 85% of fatty acids, 5.6 l of a 5% by weight aqueous solution of glycerol and 1.5 g of the same enzyme as the one used in Example 5 were introduced into a reaction vessel 31 and soybean oil and water were supplied thereto with a pump 38 at a rate of 0.15 l/hr and with a pump 39 at a rate of 0.28 l/hr, respectively. The theoretical residence time in the reaction vessel was 20 hours. The reaction was continued while stirring at 30° C. by continuously withdrawing the same amounts of the fatty acid solution and aqueous solution of glycerol formed by the reaction as those of the supplied oil and water respectively in the same manner as in Example 7.

The hydrolysis ratio of the oil and the glycerol concentration in the aqueous phase were determined 20, 40 and 60 hours after the start of the hydrolyzed reaction. Table 9 shows the results.

TABLE 9

| Reaction period (hr) | 20 | 40 | 60 |
|---|---|---|---|
| Hydrolysis ratio (%) | 86 | 61 | 38 |
| Glycerol concentration (%) | 5 | 3 | 2 |

Thus when the glycerol concentration was adjusted to 5% by weight, the hydrolysis ratio of the oil exhibited a decrease accompanied by a decrease in the glycerol concentration, which made it impossible to maintain the glycerol concentration of 5% by weight.

COMPARATIVE EXAMPLE 3

In this Comparative Example, the glycerol concentration was adjusted to 50% by weight.

The same reaction system as the one described in Example 7 was employed. 3 l of hydrolyzed fatty acids containing 85% of fatty acids, 0.7 l of 50% by weight of glycerol and 1.5 g of the same enzyme as that used in Example 5 were introduced into a reaction vessel 31. Soybean oil and water were added thereto with a pump 38 at a rate of 0.15 l/hr and with a pump 9 at a rate of 0.035 l/hr, respectively, while stirring at 30° C. The theoretical residence time in the reaction vessel was 20 hours.

As shown in FIG. 4, the same amounts of a fatty acid solution and an aqueous solution of glycerol as those of the supplied oil and water, respectively, were continuously withdrawn from the reaction system with the use of membranes.

The hydrolysis ratio of the oil and the glycerol concentration in the aqueous phase were determined 20, 40, 60 and 80 hours after the start of the hydrolysis reaction. Table 10 shows the results.

TABLE 10

| Reaction period (hr) | 20 | 40 | 60 | 80 |
|---|---|---|---|---|
| Hydrolysis ratio (%) | 72 | 69 | 68 | 68 |
| Glycerol concentration (%) | 40 | 37 | 37 | 37 |

Thus the hydrolysis ratio of the oil was low, i.e. approximately 70%, when the glycerol concentration was 50% by weight.

EXAMPLE 8

A continuous reaction was carried out in the same reaction system as the one described in Example 7 with the use of beef tallow as a fat or oil at a temperature of 50° C. which was higher than the melting point of the beef tallow.

Similar to Example 7, 3 l of hydrolyzed fatty acids containing 85% of fatty acids, 2 l of a 15% by weight aqueous solution of glycerol and 4.5 g of the same enzyme as that used in Example 5 were introduced into a reaction vessel 31 and mixed together by stirring at 50° C. Beef tallow and water maintained at 50° C. were supplied thereto with a pump 38 at a rate of 0.15 l/hr and with a pump 39 at a rate of 0.1 l/hr, respectively, thus giving a theoretical residence time in the vessel of 20 hours. The reaction was continued at 50° C. On the other hand, an aqueous solution of glycerol and a fatty acid solution were separated from the emulsion in the reaction vessel 31 with membranes 35 and 34, respectively. The remaining emulsion was returned to the reaction vessel 31. The average permeation rate of the fatty acid solution through the membrane 34 was 0.16 l/hr, while that of the aqueous solution of glycerol through the membrane 35 was 1.9 l/hr. Similar to Example 7, the solution permeating through the membrane 35 contained the enzyme which was thus collected with an ultrafiltration membrane 36. The solutions permeating through the membrane 34 and 36 were withdrawn at the same rates as those at the pumps 38 and 39, respectively, by controlling pumps 42 and 41 and a valve 46.

Thus the reaction was continued to thereby give hydrolysis ratios as shown in Table 11.

TABLE 11

| Reaction period (hr) | 20 | 40 | 60 | 120 |
|---|---|---|---|---|
| Hydrolysis ratio (%) | 91 | 90 | 91 | 91 |
| Glycerol concentration (%) | 15 | 15 | 15 | 15 |

Thus the enzyme was not inactivated at a high temperature, i.e. 50° C., when beef tallow was used as a fat or oil, thus stably maintaining a high hydrolysis ratio for a long period of time.

EXAMPLE 9

In this Example, olive oil was employed as an oil and the oil and water were semicontinuously supplied in portions while the withdrawal was similarly performed semicontinuously.

3 l of hydrolyzed fatty acids containing 85% of fatty acids, 2 l of a 15% by weight aqueous solution of glycerol and 1.5 g of the same enzyme as the one used in Example 5 were introduced into a reaction vessel and mixed together therein by stirring at 30° C. 0.15 l of olive oil and 0.1 l of water were added thereto once an hour. On the other hand, approximately 0.5 l of emulsion was collected from the reaction vessel once an hour while stirring at 30° C. The collected emulsion was centrifuged at 8000 rpm for ten min. Thus the emulsion was divided into the top (oily), medium (emulsion) and bottom (aqueous) phases. Then a 0.15 l aliquot of the oily phase comprising a fatty acid solution and a 0.12 l aliquot of the aqueous phase comprising a glycerol solution were taken out and the residual oily and aqueous phases and the whole emulsion phase were returned to the reaction vessel.

The aqueous phase was further treated with a polyacrylonitrile ultrafiltration membrane having a fractionating molecular weight of 20000 to thereby recover the enzyme. The membrane used herein was a flat membrane showing an average permeation rate of 0.4 l/hr under a pressure of 1.0 kg/cm² and a membrane area of 162 cm². A 0.1 l aliquot of the aqueous phase among 0.12 l was obtained as a permeable solution through the ultrafiltration membrane while the residue, i.e. 0.02 l, was returned to the reaction vessel as an enzyme concentrate.

Thus the reaction was continued by supplying the oil and water, withdrawing the formed fatty acid solution and aqueous solution of glycerol and ultrafiltering the aqueous solution of glycerol each once an hour.

The hydrolysis ratio of the oil and the glycerol concentration were determined 20, 40, 60 and 100 hours after the start of the hydrolysis reaction. Table 12 shows the results.

TABLE 12

| Reaction period (hr) | 20 | 40 | 60 | 100 |
|---|---|---|---|---|
| Hydrolysis ratio (%) | 92 | 93 | 92 | 92 |
| Glycerol concentration (%) | 15 | 16 | 16 | 16 |

Thus the enzyme was not inactivated when both of the supply and the withdrawal were semicontinuously performed and the reaction could be continued at a high hydrolysis ratio.

EXAMPLE 10

In Example 9, the oil and water were semicontinuously supplied. On the other hand, they were continuously supplied while the fatty acid solution and aqueous solution of glycerol formed by the reaction were semicontinuously withdrawn in this Example.

That is, hydrolyzed fatty acids, a 15% by weight aqueous solution of glycerol and an enzyme were mixed together by stirring similar to Example 9 and 0.15 l/hr of olive oil and 0.1 l/hr of water were continuously added thereto with pumps. The mixture was stirred at 30° C. to thereby perform the reaction. The fatty acid solution and aqueous solution of glycerol formed by the reaction were withdrawn once an hour at a rate of 0.15 l/hr and 0.1 l/hr, respectively, by centrifuging in the same manner as in Example 9.

Thus the reaction was continued and the hydrolysis ratio of the oil and the glycerol concentration in the aqueous phase were determined 20, 40, 60 and 100 hours after the start of the hydrolysis reaction. Table 13 shows the results which are almost the same as those of Example 9.

TABLE 13

| Reaction period (hr) | 20 | 40 | 60 | 100 |
|---|---|---|---|---|
| Hydrolysis ratio (%) | 92 | 92 | 91 | 91 |
| Glycerol concentration (%) | 15 | 16 | 15 | 15 |

Thus this reaction could be carried out by combining the continuous supply with the semicontinuous withdrawal.

The embodiments of the invention in which an exclusive property or privilege is claimed are defined as follows:

1. A process for enzymatically hydrolyzing a fat or oil with water, in the presence of a lipase, utilizing a reactor having an upper baffle, a lower baffle, means defining an intermediate zone between said upper and lower baffles and means for agitating the contents of said intermediate zone, which process comprises the steps of: continuously or semicontinuously feeding (1) the fat or oil at a first rate, and (2) water at a second rate, into said intermediate zone of said reactor which zone contains said lipase, said first rate and said second rate satisfying the following relationship $$\frac{\frac{X}{M} \cdot \frac{\eta}{100} \cdot 92}{Y - 3 \cdot \frac{X}{M} \cdot \frac{\eta}{100} \cdot 18} = 0.10 \text{ to } 0.40$$

wherein
X(kg/hr) = said first rate
Y(kg/hr) = said second rate
η(%) = decomposition ratio of fat or oil
M = molecular weight of fat or oil
18 = molecular weight of water
92 = molecular weight of glycerol, and the ratio of the volume of said oil phase in said reactor to the volumetric supply rate at which said oil or fat is supplied to said reactor being such that the residence time of said oil or fat in said reactor is at least 10 hours, agitating the contents of said intermediate zone to form an emulsion layer of (1) said fat or oil and (2) water in said intermediate zone under conditions effective to enzymatically hydrolyze the fat or oil, separating from said emulsion layer an oil phase containing hydrolyzed fatty acid which moves upwardly to a first location above said upper baffle and an aqueous phase containing glycerol and said lipase which moves downwardly to a second location below said lower baffle; continuously or semicontinuously removing said oil phase, at said first rate, from said first location above said upper baffle; continuously or semicontinuously removing said aqueous phase containing glycerol and said lipase, at said second rate, from said second location below said lower baffle, and flowing said aqueous phase through an ultrafiltration membrane under conditions effective to separate the lipase in said aqueous phase and then returning the lipase to said reactor, whereby to recover separately said oil phase containing fatty acid and said aqueous phase containing glycerol.

2. A process as claimed in claim 1 in which said oil phase consists of soybean oil and the glycerol concentration in the aqueous phase is from 18 to 20%.

3. A process as claimed in claim 1, in which the glycerol concentration in said aqueous phase is maintained substantially constant throughout the reaction, and said concentration is within the range of from 10 to 40% by weight.

4. A process as claimed in claim 1, in which said intermediate zone comprises a draft tube and said means for agitating the contents of said intermediate zone comprise stirring blades in said draft tube.

5. A process as claimed in claim 1, in which said means for agitating the contents of said intermediate zone comprise conduit means for blowing an inert gas into the lower portion of said intermediate zone in order to urge said aqueous layer to rise in said intermediate zone.

* * * * *